US008563266B2

(12) United States Patent
Shigematsu et al.

(10) Patent No.: US 8,563,266 B2
(45) Date of Patent: Oct. 22, 2013

(54) A-87774 COMPOUNDS OR SALTS THEREOF, PRODUCTION METHOD THEREOF AND AGROCHEMICALS CONTAINING THE SAME AS ACTIVE INGREDIENT (75) Inventors: Yoshio Shigematsu, Konan (JP); Yoshiko Sugie, Otsu (JP); Masaaki Kizuka, Tsuchiura (JP)

(73) Assignee: Mitsui Chemicals Agro, Inc., Minato-Ku, Tokyo (JP)

( * ) Notice: Subject to any disclaimer, the term of this patent is extended or adjusted under 35 U.S.C. 154(b) by 9 days.

(21) Appl. No.: 13/390,817

(22) PCT Filed: Aug. 13, 2010

(86) PCT No.: PCT/JP2010/063744
§ 371 (c)(1),
(2), (4) Date: Feb. 16, 2012

(87) PCT Pub. No.: WO2011/021580
PCT Pub. Date: Feb. 24, 2011

(65) Prior Publication Data
US 2012/0149575 A1 Jun. 14, 2012

(30) Foreign Application Priority Data
Aug. 18, 2009 (JP) .................. 2009-188988

(51) Int. Cl.
*C12P 1/00* (2006.01)
*C12P 13/00* (2006.01)
*C12P 11/00* (2006.01)
*C12P 7/00* (2006.01)
*C12N 1/20* (2006.01)
*A01N 57/00* (2006.01)

(52) U.S. Cl.
USPC ............. 435/41; 435/128; 435/130; 435/132; 435/253.5; 504/194

(58) Field of Classification Search
USPC .......... 504/194; 435/41, 128, 130, 132, 253.5
See application file for complete search history.

(56) References Cited

U.S. PATENT DOCUMENTS

| 4,952,234 A | 8/1990 | Haneishi et al. |
| 5,401,709 A | 3/1995 | Andriollo et al. |

FOREIGN PATENT DOCUMENTS

| JP | 56-030907 A | 3/1981 |
| JP | 62-012789 A | 1/1987 |

(Continued)

OTHER PUBLICATIONS

Compiled Abstracts from JP-02215791A; JP 04120005A; JP-05262776A; JP-07067676A; Kim et all., 1993, J. of Microbiology and Biotechnology, 3(1):51-60; Takahashi et al., 1994, ACS Symposium Series, 551:74-84; Nakajima et al., 1991, The J. of Antibiotics, 44(3):293-300; all in SciFiinder Search Results for U.S. Appl. No. 13/390,817, downloaded Jun. 7, 2013.*

(Continued)

*Primary Examiner* — Jane C Oswecki
(74) *Attorney, Agent, or Firm* — Buchanan Ingersoll & Rooney PC (57) ABSTRACT There are provided novel A-87774 compounds or salts thereof having a herbicidal activity or a plant growth regulating activity, a microorganism producing the same, a production method thereof, an agrochemical (in particular, herbicide or plant growth regulator) containing the same as an active ingredient, a method for using the same, and a culture of the microorganism.

8 Claims, 5 Drawing Sheets

(56) References Cited

FOREIGN PATENT DOCUMENTS

| JP | 2-215791 | A | | 8/1990 |
|---|---|---|---|---|
| JP | 5-025189 | A | | 2/1993 |
| JP | 5-168485 | A | | 7/1993 |
| JP | 05-279375 | | * | 10/1993 |
| JP | 5-279375 | A | | 10/1993 |
| JP | 5-294982 | A | | 11/1993 |
| JP | 6-256324 | A | | 9/1994 |
| JP | 9-194499 | A | | 7/1997 |

OTHER PUBLICATIONS

International Search Report (PCT/ISA/210) issued on Sep. 28, 2010, by Japanese Patent Office as the International Searching Authority for International Application No. PCT/JP2010/063744.

Written Opinion (PCT/ISA/237) issued on Sep. 28, 2010, by Japanese Patent Office as the International Searching Authority for International Application No. PCT/JP2010/063744.

* cited by examiner

A-87774 COMPOUNDS OR SALTS THEREOF, PRODUCTION METHOD THEREOF AND AGROCHEMICALS CONTAINING THE SAME AS ACTIVE INGREDIENT

TECHNICAL FIELD

The present invention relates to A-87774 compounds or salts thereof, a microorganism producing the same, a production method thereof, an agrochemical (in particular, herbicide or plant growth regulator) containing the same as an active ingredient, a method for using the same, and a culture product of the microorganism.

BACKGROUND ART

Microorganisms produce various physiologically active substances, and a part of them has been utilized effectively for the improvement of productivity in the field of agriculture. For example, milbemycins, avermectins, and spinosyns have been put into practical use as insecticides, and blasticidin and kasugamycin as fungicides.

On the other hand, in the field of herbicides, bialaphos has been commercialized.

Metabolites of microorganisms, when used as agrochemicals, have an advantage of being easily degraded in the environment, and this advantage is deemed to be a desirable property which the future agrochemicals should have, in consideration of the environmental load. However, no compound has been put into practical use other than those set forth above as a compound having a herbicidal activity, and there have been demands for a novel active substance to be produced.

SUMMARY OF THE INVENTION

Problems to be Solved by the Invention

An object of the invention is to provide novel A-87774 compounds or salts thereof having a herbicidal activity or a plant growth regulating activity, a microorganism producing the same, a production method thereof, an agrochemical (in particular, herbicide or plant growth regulator) containing the same as an active ingredient, a method for using the same, and a culture product of the microorganism.

Means for Solving the Problems

The present inventors, in light of the aforementioned problems, have intensively conducted research on metabolites of microorganisms, and as a result have found that compounds having an extremely strong herbicidal activity are present in a culture solution of microorganisms belonging to *Streptomyces*, which has led to the completion of the present invention.

That is, the present invention provides A-87774 compounds represented by A-87774-1, A-87774-2 or A-87774-3 or a salt thereof, a microorganism producing the compound, a production method of the compound, an agrochemical (in particular, herbicide or plant growth regulator) containing the compound as an active ingredient, a method for weeding using the compound and a method for regulating plant growth, a culture product obtainable by culturing the microorganisms, and an agrochemical containing the culture product.

Effect of the Invention

The novel A-87774 compounds of the present invention have an excellent herbicidal action or plant growth regulating action, and are useful as an agrochemical (in particular, herbicide or a plant growth regulator).

MODE FOR CARRYING OUT THE INVENTION

The novel compound A-87774-1 of the present invention has the following properties:

1) Molecular weight: 668,
2) Molecular formula: $C_{18}H_{29}N_4O_{17}PS_2$,
3) $^1$H-nuclear magnetic resonance spectrum ($\delta_{ppm}$) when measured in deuterated water: 5.86 (1H, d, J=5.9 Hz), 5.59 (1H, d, J=11.0 Hz), 4.56 (1H, q, J=6.9 Hz), 4.42 (1H, dd, J=11.2, 2.9 Hz), 4.38 (1H, dd, J=11.2, 3.7 Hz), 4.30-4.27 (2H, m), 4.24-4.23 (2H, m), 4.07 (1H, d, J=10.1 Hz), 3.97 (1H, dd, J=12.7, 2.1 Hz), 3.61 (1H, dd, J=11.3, 10.3 Hz), 3.55 (1H, m), 3.52 (1H, m), 3.33 (1H, dd, J=11.4, 1.8 Hz), 2.72 (1H, dd, J=7.0, 6.6 Hz), 1.42 (3H, d, J=6.9 Hz),
4) $^{13}$C-nuclear magnetic resonance spectrum ($\delta_{ppm}$) when measured in deuterated water: 178.6 (s), 174.0 (s), 154.8 (s), 91.4 (s), 89.2 (d), 87.6 (d), 80.8 (d), 74.8 (d), 73.5 (d), 70.2 (d), 70.2 (d), 70.0 (t), 63.7 (d), 60.6 (d), 53.8 (t), 36.5 (t), 30.3 (t), 18.3 (q),
5) Infrared absorption spectrum ($v_{max}$cm$^{-1}$) when measured by KBr disc: 3423, 1703, 1639, 1487, 1450, 1406, 1383, 1339, 1258, 1217, 1184, 1088, 1067, 937, 899, 827, 536, and
6) Specific optical rotation: $[\alpha]_D^{24}$+40.0° (c, 0.22, in H$_2$O).

The novel compound A-87774-2 of the present invention has the following properties:

1) Molecular weight: 666,
2) Molecular formula: $C_{18}H_{27}N_4O_{17}PS_2$,
3) $^1$H-nuclear magnetic resonance spectrum ($\delta_{ppm}$) when measured in deuterated water: 7.73 (1H, d, J=8.1 Hz), 5.91 (1H, d, J=2.4 Hz), 5.90 (1H, d, J=8.1 Hz), 5.60 (1H, d, J=10.8 Hz), 4.57 (1H, q, J=6.9 Hz), 4.55 (1H, d, J=11.4 Hz), 4.46 (1H, dd, J=11.2, 2.2 Hz), 4.34-4.32 (3H, m), 4.22 (1H, d, J=12.6 Hz), 4.07 (1H, d, J=10.1 Hz), 3.96 (1H, dd, J=12.6, 1.7 Hz), 3.61 (1H, dd, J=11.4, 10.1 Hz), 3.32 (1H, d, J=11.4 Hz), 1.42 (3H, d, J=6.9 Hz),
4) $^{13}$C-nuclear magnetic resonance spectrum ($\delta_{ppm}$) when measured in deuterated water: 178.6 (s), 166.3 (s), 151.8 (s), 141.7 (d), 102.8 (d), 91.3 (s), 89.3 (d), 89.2 (d), 81.5 (d), 74.8 (d), 73.5 (d), 73.4 (d), 69.5 (d), 69.4 (t), 63.7 (d), 60.6 (d), 53.8 (t), 18.3 (q), 5) Infrared absorption spectrum ($v_{max}$cm$^{-1}$) when measured by KBr disc: 3399, 1706, 1455, 1405, 1346, 1266, 1185, 1087, 1067, 934, 900, 826, 534, and 6) Specific optical rotation: $[\alpha]_D^{24}$+47.2° (c, 1.0, in H$_2$O).

The novel compound A-87774-3 of the present invention has the following properties:

1) Molecular weight: 828,
2) Molecular formula: $C_{24}H_{37}N_4O_{22}PS_2$,
3) $^1$H-nuclear magnetic resonance spectrum ($\delta_{ppm}$) when measured in deuterated water: 7.74 (1H, d, J=8.1 Hz), 5.94 (1H, d, J=5.3 Hz), 5.91 (1H, d, J=8.1 Hz), 5.60 (1H, d, J=11.0 Hz), 5.01 (1H, br.s), 4.57 (1H, q, J=6.9 Hz), 4.57 (1H, m), 4.50-4.48 (3H, m), 4.41 (1H, m), 4.22 (1H, d, J=12.5 Hz), 4.07 (1H, d, J=10.1 Hz), 4.04 (1H, dd, J=3.3, 1.8 Hz), 3.96 (1H, dd, J=12.5, 1.3 Hz), 3.87 (1H, d, J=12.3 Hz), 3.85 (1H, m), 3.71 (1H, dd, J=12.3, 4.4 Hz), 3.63-3.61 (3H, m), 3.32 (1H, d, J=11.4 Hz), 1.42 (3H, d, J=6.9 Hz),
4) $^{13}$C-nuclear magnetic resonance spectrum ($\delta_{ppm}$) when measured in deuterated water: 178.6 (s), 166.3 (s), 151.8 (s), 141.6 (d), 102.9 (d), 100.3 (d), 91.3 (s), 89.2 (d), 89.1 (d), 80.2 (d), 74.8 (d), 74.1 (d), 73.8 (d), 73.5 (d), 72.2 (d), 70.3 (d), 69.9 (d), 69.3 (t), 66.8 (d), 63.7 (d), 61.0 (t), 60.6 (d), 53.7 (t), 18.3 (q),
5) Infrared absorption spectrum ($v_{max}$cm$^1$) when measured by KBr disc: 3396, 1705, 1402, 1340, 1265, 1184, 1090, 1063, 937, 899, 825, 538, and
6) Specific optical rotation: $[\alpha]_D^{24}$+78.7° (c, 1.0, in H$_2$O).

A-87774 compounds can form any salts as long as they do not impair the herbicidal action or plant growth regulating action of A-87774 compounds. Salts of A-87774 compounds, for example, may be salts with an alkaline metal or an alkaline earth metal such as a sodium salt, a potassium salt, a magnesium salt and a calcium salt; ammonium salts; or salts with an organic amine such as an isopropylamine and triethylamine, and preferably a sodium salt.

By culturing microorganisms, A-87774 compounds of the present invention can be isolated from the culture product thereof.

Examples of strains belonging to *Streptomyces* genus used in the production method of A-87774 compounds of the present invention can include *Streptomyces* sp. strain SANK 61805. The mycological feature of strain SANK 61805 is as follows. It should be noted that the taxonomic analysis such as morphological property, properties on various culture media, physiological property, chemotaxonomic property and 16S rRNA gene of strain SANK 61805 followed the method described in "Identification Manual of Actinomycetes (Hosenkin no Bunrui to Dotei)" (edited by The Society for Actinomycetes Japan, published by Business Center for Academic Societies Japan, 2001).

1. Morphological Feature

Strain SANK 61805 was cultured on an agar medium defined by ISP (International *Streptomyces* Project) at 28° C. for 14 days, followed by microscopic observation. Substrate mycelia elongates well and branches, and exhibits pale yellowish brown, yellowish brown to grayish yellow brown color. *Nocardia* genus strain-like mycelia rupture or zigzag elongation is not observed. Aerial mycelia branches simply, and exhibits white, brownish gray to grayish yellow brown color. 10 to 50 or more of spore chains are formed at the tip of the aerial mycelia, and the spore chains exhibit a linear form or, on rare occasions, a spiral form. Scanning electron microscopic observation exhibits smooth surface structure. The spore is elliptical and has a size of 0.4 to 0.8×0.8 to 1.2 μm. Further, a special organ such as trochoid branch sclerotium or sporangium of aerial mycelia is not observed.

2. Properties on Various Culture Media

On various culture media, properties after culturing at 28° C. for 14 days are shown in Table 1. Color tone indications represent color chip numbers in "Standard Color Chart" issued by Japan Color Research Institute according to Munsell system.

TABLE 1

| Types of media | Items [1] | Properties of strain SANK 61805 |
|---|---|---|
| Yeast extract/malt extract agar (ISP2) | G | Very good, elevated, dull yellow orange (10YR7/8) [2] |
| | AM | Abundantly formed, velvety, dark brownish gray (5YR4/2) |
| | R | Dull yellow orange (10YR7/10) |
| | SP | Not produced |
| Oatmeal agar (ISP3) | G | Very good, elevated, colorless |
| | AM | Abundantly formed, velvety, grayish brown (5YR5/2) |
| | R | Dull yellow orange (10YR7/8) |
| | SP | Not produced |
| Starch/inorganic salt agar (ISP4) | G | Very good, elevated, yellowish brown (10YR5/4) |
| | AM | Very good, velvety, grayish brown (5YR5/2) |
| | R | Yellow brown (10YR7/6) |
| | SP | Not produced |
| Glycerin/asparagine agar (ISP5) | G | Very good, elevated, yellowish brown (10YR5/4) |
| | AM | Very good, grayish brown (5YR5/2) |
| | R | Dull yellow orange (10YR7/8) |
| | SP | Not produced |
| Peptone/yeast/iron agar (ISP6) | G | Not very good, elevated, grayish yellow brown (10YR5/3) |
| | AM | Not very good, white |
| | R | Grayish yellow brown (10YR5/3) |
| | SP | Black |
| Tyrosine agar (ISP7) | G | Very good, elevated, dark brownish gray (10YR3/1) |
| | AM | Very good, velvety, brownish gray (10YR5/2) |
| | R | Dark brownish gray (10YR2/1) |
| | SP | Black |
| Sucrose/nitrate agar | G | Not very good, elevated, colorless |
| | AM | Not very good, velvety, grayish yellow brown (10YR5/3) |
| | R | Colorless |
| | SP | Not produced |
| Glucose/asparagine agar | G | Not very good, elevated, colorless |
| | AM | Not very good, velvety, grayish yellow brown (10YR5/3) |
| | R | Colorless |
| | SP | Not produced |
| Nutritive agar (Difco) | G | Not very good, flat, pale yellowish brown (2.5Y8/4) |
| | AM | Not formed |
| | R | Pale yellowish brown (2.5Y8/4) |
| | SP | Not produced |
| Potato extract/ carrot extract agar | G | Not very good, elevated, pale yellowish brown (10YR7/3) |
| | AM | Not very good, velvety, grayish yellow brown (10YR5/3) |
| | R | Pale yellowish brown (10YR7/3) |
| | SP | Not produced |
| Water agar | G | Not good, flat, yellowish gray (7.5Y9/2) |
| | AM | Not good, velvety, grayish yellow brown (10YR5/3) |
| | R | Yellowish gray (7.5Y9/2) |
| | SP | Not produced |

[1] "G", "AM", "R" and "SP" stand for "growth", "aerial mycelia", "reverse side" and "soluble pigment", respectively.
[2] Indications within the parentheses in the column of properties are color tone indications according to Munsell system.

3. Physiological Property

The physiological properties of strain SANK 61805 observed for 2 to 21 days after culturing at 28° C. are shown in Table 2.

TABLE 2

| | | |
|---|---|---|
| Hydrolysis of starch | | positive |
| Liquefaction of gelatin | | negative |
| Reduction of nitrate | | negative |
| Peptonization of milk | | negative |
| Coagulation of milk | | negative |
| Productivity of melanine-like pigment | (medium 1) [1] | positive |
| | (medium 2) [2] | positive |
| | (medium 3) [3] | positive |
| Substrate degradability | casein | negative |
| | tyrosine | positive |
| | xanthine | negative |
| Growth temperature range | (medium 4) [4] | 10-48° C. |
| Growth proper temperature | (medium 4) | 24-40° C. |
| Salt tolerance | | 7% |

[1] "Medium 1" denotes "triptone/yeast extract/broth (ISP1)".
[2] "Medium 2" denotes "peptone/yeast extract/iron agar (ISP6)".
[3] "Medium 3" denotes "tyrosine agar (ISP7)".
[4] "Medium 4" denotes "yeast extract/malt extract agar (ISP2)".

Further, utilization of carbon sources of strain SANK 61805 observed after culturing at 28° C. for 14 days using Pridham-Gottlieb agar medium (ISP9) is shown in Table 3.

TABLE 3

| D-glucose | + | D-fructose | + |
|---|---|---|---|
| L-arabinose | + | L-rhamnose | + |
| D-xylose | + | Sucrose | − |
| Inositol | − | Raffinose | + |
| D-mannitol | + | Control | − |

"+" stands for "utilized", "±" stands for "weakly utilized", and "−" stands for "not utilized".

4. Regarding Fungal Component

The chemotaxonomic property of strain SANK 61805 was investigated according to "Identification Manual of Actinomycetes (Hosenkin no Bunrui to Dotei)" [The Society for Actinomycetes Japan (edit), Business Center for Academic Societies Japan, pp. 49-82, 2001]. As a result, LL-diaminopimelic acid was detected from the cell wall, and no characteristic pattern was observed as a sugar component in the whole cell. As major menaquinone molecular species, MK-9 ($H_6$) and MK-9 ($H_8$) were detected.

5. 16S rRNA Genetic Analysis

The base sequence (1325 bp) of 16S rRNA genes of strain SANK 61805 was decoded, and database search was carried out, resulting in strain SANK 61805 being included in a cluster of *Streptomyces* genus.

Identification was carried out in accordance with ISP (International Streptomyces Project) criteria, S. A. Waksman, The Actinomycetes, vol. 2, R. E. Buchanan and N. E. Gibbons, Bergey's Manual of Determinative Bacteriology, 8th edition, 1974, Bergey's Manual of Systematic Bacteriology, vol. 4, 1989, and recent documents concerning *Streptomyces* genus actinomycetes to determine that the present strain belongs to *Streptomyces* genus among actinomycetes. Then, the present strain was named as *Streptomyces* sp. strain SANK 61805.

From the above results, the present strain was identified as *Streptomyces* sp. strain SANK 61805 (hereinafter, in the present specification, referred to as "strain SANK 61805"). It should be noted that the present strain was internationally deposited with the National Institute of Advanced Industrial Science and Technology International Patent Organism Depositary (Address: AIST Tsukuba Central No. 6, 1-1-1 Higashi, Tsukuba, Ibaraki, Japan) as of Jun. 19, 2007, and the depository number thereof is FERM BP-10840.

As well known in the art, actinomycetes are susceptible to mutation in nature or by artificial operation (for example, ultraviolet radiation, radioactive radiation, chemical treatment, etc.), and strain SANK 61805 of the present invention is also susceptible to mutation, as well. Strain SANK 61805 of the present invention includes all the mutant strains thereof. Further, these mutant strains also include those obtained by a genetic method, for example, recombination, transduction, transformation, or the like. That is, strain SANK 61805 which produces compound A-87774-1, A-87774-2 or A-87774-3 and the mutant strain thereof, and strains which cannot be clearly distinguished therefrom are all included in strain SANK 61805.

When culturing a strain (production strain) which produces A-87774 compounds of the present invention, a medium to be used may be a medium which appropriately contains those selected from a carbon source, a nitrogen source, an inorganic ion and an organic nutritive source, and any of synthetic or natural medium may also be included.

The nutritive sources may be those which are known and conventionally used for culturing strains of mycetes and actinomycetes, and include carbon sources, nitrogen sources and inorganic salts which can be utilized by microorganisms.

Specifically, the carbon source may be, for example, glucose, fructose, maltose, sucrose, mannitol, glycerol, dextrin, oats, rye, corn starch, potato, corn flour, soybean flour, cottonseed oil, starch syrup, molasses, soybean oil, citric acid or tartaric acid, and may be used alone or in combination. The carbon source is, in general, used within, but not limited to, the range of from 1 to 10% by weight of the amount of medium.

Further, the nitrogen source may be, in general, a material containing protein or a hydrolysate thereof. Preferable nitrogen source may be, for example, soybean flour, wheat bran, peanut flour, cotton flour, skim milk, casein hydrolysate, Pharmamine, fish meal, corn steep liquor, peptone, meat extract, raw yeast, dry yeast, yeast extract, malt extract, potato, ammonium sulfate, ammonium nitrate or sodium nitrate, and may be used alone or in combination. The nitrogen source is preferably used within the range of from 0.2 to 6% by weight of the amount of medium.

Furthermore, the nutritive inorganic salt may be an ordinary salt capable of providing ions of sodium, ammonium, calcium, phosphate, sulfate, chloride or carbonate. Further, the nutritive inorganic salt may also be a trace amount of a metal such as potassium, calcium, cobalt, manganese, iron, zinc, nickel or magnesium.

It should be noted that, upon liquid culture, an antifoamer such as a silicone oil, vegetable oil or surfactant can be used.

The pH of a medium for culturing strains which produce A-87774 compounds (production strain, in particular, strain SANK 61805) to produce compound A-87774-1, A-87774-2 or A-87774-3 is preferably 5.0 to 8.0.

The temperature of a medium for producing A-87774 compounds may be appropriately modified within a range in which a production strain (production strain, in particular, strain SANK 61805) produces a desired substance, but is preferably 22 to 36° C.

A-87774 compounds can be obtained by aerobically culturing a production strain (in particular, strain SANK 61805), and obtaining them from the culture product. Such culture method may be an aerobic culture method that is usually used, for example, a solid culture method, a shaking culture method or an aeration stirring culture method.

A-87774 compounds can be extracted, by separating a culture solution of a production strain (in particular, strain SANK 61805) into a liquid and a fungal component, or without separating, from the filtrate or the culture solution, utilizing the physicochemical property thereof, and are preferably extracted after separation into a liquid and a fungal component. The separation can be carried out, for example, by a centrifugal separation method or a filtration method using diatomaceous earth as a filtration aid.

When extracting A-87774 compounds from a fungal component, an aqueous solution or a water-soluble organic solvent is added to a fungal component followed by stirring, and subsequently the mixture is subjected to, for example, a centrifugal separation method or a filtration method using diatomaceous earth as a filtration aid to separate a liquid phase. From the resulting liquid phase, a water-soluble organic solvent is distilled off (preferably, distilled off under reduced pressure), and subsequently the similar procedure to that of the filtrate of the culture solution mentioned below can be carried out to obtain compounds A-87774-1, A-87774-2 or A-87774-3. The water-soluble organic solvent for use in extraction may be methanol, ethanol, acetone, acetonitrile or tetrahydrofuran, or a mixed solvent thereof, and the ratio of the water-soluble organic solvent to be added is 0 to 95% by volume.

A-87774 compounds are a water-soluble substance, and utilization of the physicochemical property thereof allows it to be extracted and purified from the filtrate. As an adsorbent, for example, an activated carbon, or a synthetic adsorbent is used. Such synthetic adsorbent may be, for example, HP series such as Diaion HP-20 (manufactured by Mitsubishi Chemical Corporation) or XAD series such as AMBERLITE XAD-2 (manufactured by Organo Corporation). The liquid containing A-87774 compounds may be passed through the adsorbent layer as mentioned above to remove therefrom impurities contained therein by adsorption, or A-87774 compounds may also be adsorbed thereto once and subsequently eluted with an organic solvent. The elution organic solvent may be, for example, a water-soluble organic solvent such as methanol, ethanol, acetone, acetonitrile or tetrahydrofuran, and a mixed solvent of water and such water-soluble organic solvent, and in addition a solvent having the pH adjusted by the addition of acetic acid, formic acid or aqueous ammonia may also be used. Further, it is also possible to extract or remove impurities contained in an aqueous solution containing A-87774 compounds, using a water-immiscible organic solvent, for example, ethyl acetate, toluene, chloroform, methylene chloride, butanol, or the like, alone or in combination, without using an adsorbent.

The extraction fraction of A-87774 compounds thus obtained can be subjected to an ordinary method used for purification of an organic compound for further purification. Such purification method may be, for example, adsorption, partition, cation exchange, anion exchange, gel filtration column chromatography, thin layer chromatography or high performance liquid chromatography. The carrier for use in these chromatography may be, for example, silica gel, alumina, florisil, cellulose, activated carbon, Dowex 50W, Amberlite CG-400, Sephadex LH-20, Sephadex G-25 or silica gel C18, and these can be used alone or in combination in any order to isolate and purify A-87774 compounds effectively.

A-87774 compounds of the present invention obtained from a culture product which can be obtained by culturing a production strain (in particular, strain SANK 61805) as mentioned above have an excellent herbicidal activity, and thus can be used, as an agrochemical, in particular, as a herbicide, for removing harmful weeds in the field of agriculture and horticulture, in particular weeds in upland fields or weeds in paddy fields, by treating weeds or soil.

Such harmful weeds in upland fields may be, for example, solanaceous weeds such as black nightshade and thorn apple, malvaceous weeds such as velvetleaf and prickly sida, convolvulaceous weeds such as tall morning glory and field bindweed, amaranthaceous weeds such as livid amaranth and redroot pigweed, asteraceous weeds such as common cocklebur, common ragweed, common groundsel and annual fleabane, cruciferous weeds such as wild mustard and shepherd's-purse, chenopodiaceous weeds such as common lambsquarters and figleaved goosefoot, violaceous weeds such as field pansy, caryophyllaceous weeds such as common chickweed, leguminous weeds such as white clover, Indian jointvetch and sicklepod, portulacaceous weeds such as common purslane, scrophulariaceous weeds such as Persian speedwell, lamiaceous weeds such as henbit, euphorbiaceous weeds such as prostrate spurge, graminaceous weeds such as barnyard grass, johnsongrass, southern crabgrass, goosegrass, annual bluegrass, water foxtail, wild oat, stiff darnel, ryegrass, green foxtail and bermudagrass, cyperaceous weeds such as rice flatsedge and yellow nutsedge, commelinaceous weeds such as asiatic dayflower and tropical spiderwort, or equisetaceous weeds such as field horsetail. Further, harmful weeds in paddy field may be graminaceous weeds such as early watergrass, cyperaceous weeds such as Japanese bulrush, tidalmarsh flatsedge, needle spikerush, Kuroguwai and Shizui, alismataceous weeds such as arrowhead and dwarf arrowhead, or broadleaf weeds such as common falsepimpernel, heartshape false pickerelweed, Indian toothcup and three-stamen waterwort.

The herbicidal activity of A-87774 compounds over these weeds can be evaluated by treating stem and leave portions with a drug solution after germination of target weeds, or by treating soil in which seeds or tubers of target weeds are present with a drug solution before germination of target weeds, and comparing the subsequent growth of the weeds with that of the untreated control group.

A-87774 compounds can be used not only for farm land and paddy fields, but also for orchards, mulberry fields, non-agricultural lands and mountain forests.

Furthermore, A-87774 compounds of the present invention also have an activity of regulating or suppressing the growth thereof without allowing plants to be withered to death, and thus are used as a plant growth regulator. A plant body can be treated with A-87774 compounds at an appropriate time and concentration to regulate the growth of plants, and thus various efficacies can be expected such as, for example, prevention of lodging due to shortened paddy rice stem, and reduced number of trimming due to grass growth suppression.

A-87774 compounds can be applied in a form of formulation commonly used as an agrochemical formulation. Such formulation may be, for example, emulsions, wettable powders, granulated wettable powders, water soluble chemicals, solutions, powders, granules, suspensions, flowables, dry flowables, or capsules by polymer materials.

These formulations may contain appropriate additives and carriers, and such additives and carriers to be contained in a solid formulation may be, for example, vegetable powders such as soy flour, wheat flour, starch and crystal cellulose; mineral powders such as diatomaceous earth, phosphorite, gypsum, talc, bentonite, zeolite and clay; or organic or inorganic compounds such as sodium benzoate, urea, calcium carbonate and sodium sulfate. Further, the additive and carrier to be contained in a liquid formulation may be, for example, vegetable oils such as soybean oil, rapeseed oil and cottonseed oil; mineral oils; aromatic hydrocarbons such as kerosene, xylene and toluene; amides such as formamide and dimethylformamide; esters such as ethylene glycol acetate and diethyl succinate; ketones such as methyl isobutyl ketone and acetone; ethers such as ethylene glycol ethyl ether; alcohols such as ethylene glycol and isopropanol; dimethyl sulfoxide; trichloroethylene; or water. A surfactant may be added in order to make the liquid formulation uniform and stable.

The appropriate non-ionic surfactant may be, for example, an ethylene oxide polymer adduct of higher aliphatic alcohols such as fatty acid sucrose ester, lauryl alcohol, stearyl alcohol and oleyl alcohol; an ethylene oxide polymer adduct of alkyl phenols such as isooctyl phenol and nonyl phenol; an ethylene oxide polymer adduct of alkyl naphthols such as butyl naphthol and octyl naphthol; an ethylene oxide polymer adduct of higher fatty acids such as palmitic acid, stearic acid and oleic acid; an ethylene oxide polymer adduct of mono- or di-alkyl phosphates such as stearyl phosphate and dilauryl phosphate; an ethylene oxide polymer adduct of higher aliphatic amines such as dodecylamine and stearamide; a higher fatty acid ester of polyvalent alcohols such as sorbitan; and an ethylene oxide polymer adduct thereof as well as a copolymer of ethylene oxide and propylene oxide.

The appropriate anionic surfactant may be, for example, salts of alkyl sulfuric acid such as sodium lauryl sulfate and amine salts of oleyl alcohol sulfuric acid ester; salts of fatty acid such as sodium dioctylsulfosuccinate, sodium oleate and sodium stearate; or alkylaryl sulfonates such as sodium isopropylnaphthalene sulfonate, sodium methylene bisnaphthalene sulfonate, sodium ligninsulfonate and sodium dodecylbenzenesulfonate. Further, the appropriate cationic surfactant may be, for example, a higher aliphatic amine, quaternary ammonium salts, or alkyl pyridinium salts.

The content of A-87774 compounds in an agrochemical formulation depends on dosage forms, or the like, but is, for example, 100% by weight as the upper limit, and 0.01% by weight as the lower limit, preferably, 0.1 to 50% by weight. The amount of A-87774 compounds to be applied as an agrochemical depends on target weeds, target plants to be regulated in the growth thereof, dosage forms, or the contents in preparations, but may be 1000 g to 0.1 g per 10 ares, preferably, within the range of from 100 g to 1 g.

In the following, the present invention will be explained in more detail with reference to Examples and Test Examples, but the present invention is not limited thereto.

EXAMPLES

Example 1

Separation of Compounds A-87774-1 and A-87774-2
(1) Culture of Strain SANK 61805

80 mL of a medium as shown in the following medium composition was put into a 500 mL volume Erlenmeyer flask, and heated and sterilized at 121° C. for 30 minutes. To each medium, one platinum loop of *Streptomyces* sp. strain SANK 61805 was inoculated from a slant, and cultured at 28° C. and at 210 rpm for 3 days under rotational shaking to give a seed culture solution. 80 mL of a medium having the same composition was put into 100 of 500 mL volume Erlenmeyer flasks each, and heated and sterilized at 121° C. for 30 minutes, which was cooled to room temperature. To this, 0.5 mL of the aforementioned seed culture solution was inoculated, and cultured at 28° C. and at 210 rpm for 8 days under rotational shaking.

| Medium composition | |
|---|---|
| Soluble starch | 40 g |
| Glucose | 10 g |
| Soy flour | 10 g |
| Yeast extract | 4.5 g |
| Corn steep liquor | 2.5 g |
| Potassium dihydrogen phosphate | 0.5 g |
| Magnesium phosphate octahydrate | 0.05 g |
| Zinc sulfate heptahydrate | 0.01 g |
| Nickel sulfate hexahydrate | 0.001 g |
| Cobalt chloride hexahydrate | 0.001 g |
| CB-442 (antifoamer) | 0.05 g |
| Tap water | 1000 mL |
| pH before sterilization | 7.5 |

(2) Separation of Compounds A-87774-1 and A-87774-2

Separation of active ingredients was carried out according to the following method. Upon separation, wild mustard cultivated for 7 days in paddy field soil placed in a 4 cm cube pot was sprayed with a 0.5 mL solution of each fraction, and the active ingredients were investigated according to herbicidal effects thereof.

8 L of the culture solution obtained in the above (1) was separated into a fungal component and a liquid portion by a centrifuge (7500×g). The fungal component portion was stirred together with methanol, and subsequently filtered on diatomaceous earth. After the filtrate was concentrated under reduced pressure, it was combined with the liquid portion of the culture solution and concentrated to 5 L, which was passed through Diaion HP-20 column (inner diameter 6 cm, length 31 cm), and the passed liquid and 2.8 L water used to wash the column were combined. This solution was passed through Dowex 50W×8 column ($H^+$ type: inner diameter 6 cm, length 33 cm), and the passed solution and 2 L water used to wash the column were combined. Then, this solution was passed through the activated carbon column (inner diameter 6 cm, length 20 cm) to adsorb the active ingredient. The column was washed with 1 L water, and 2 L methanol/water (3/1), and subsequently the active ingredient was eluted with 2.5 L methanol/2.8% aqueous ammonia (4/1). The solid product obtained from the eluate by distilling off the solvent under reduced pressure was dissolved in 80 mL water, and passed through Amberlite CG-400 type I column ($Cl^-$ type: inner diameter 4 cm, length 22 cm). The column was washed sequentially with 1 L of 0.02N-HCl, and 1 L of 0.02N-HCl containing 0.01M-NaCl, and subsequently the active ingredient was eluted with 1.3 L of 0.02N-HCl containing 0.6M-NaCl. In order to remove NaCl, this was passed through the activated carbon column (inner diameter 3 cm, length 20 cm) again, and the column was washed with 1 L water, and subsequently the active ingredient was eluted with 1.5 L methanol/2.8% aqueous ammonia (4/1), and distilled off the solvent under reduced pressure to give 383 mg of the solid product.

This solid product was purified by Sephadex G-25 column chromatography. That is, into Sephadex G-25 column (inner diameter 2.5 cm, length 41 cm) equilibrated with a mixed solvent of acetonitrile, water and acetic acid (volume mixing ratio: 73/27/0.1), the solid product was placed after dissolution in 1 mL water, and eluted with the same mixed solvent, and the eluate was fractionated into 12 mL each portion. The active ingredient having herbicidal activity was eluted from 49th to 89th portions, and thus the solvent of this fraction was distilled off under reduced pressure to give 130 mg of the solid product.

This solid product was purified by high performance liquid chromatography (HPLC). As the HPLC column, Shiseido CAPCELL-PAK C18 UG120 Å (inner diameter 2 cm, length 25 cm) was used, and as the eluent, a mixed solvent of acetonitrile, water and acetic acid (volume mixing ratio: 4/96/0.1) was used, to carry out elution at a column oven temperature of 40° C., and at a flow rate of 15 mL/min, giving 11.3 mg of compound A-87774-2 as a white powder eluted at a retention time between 5.6 and 9.6 minutes and 81.3 mg of a fraction containing compound A-87774-1 eluted before 5.6 minutes. The latter was purified again with Shiseido CAPCELL-PAK C18 UG120 Å (inner diameter 1 cm, length 25 cm) and with HPLC (column oven temperature 40° C., flow rate 5 mL/min) using a mixed solvent of acetonitrile, water and acetic acid (volume mixing ratio: 3/97/0.1) to give 2.4 mg of compound A-87774-1 as a white powder eluted between 13.4 and 16.6 minutes.

Figure 1:
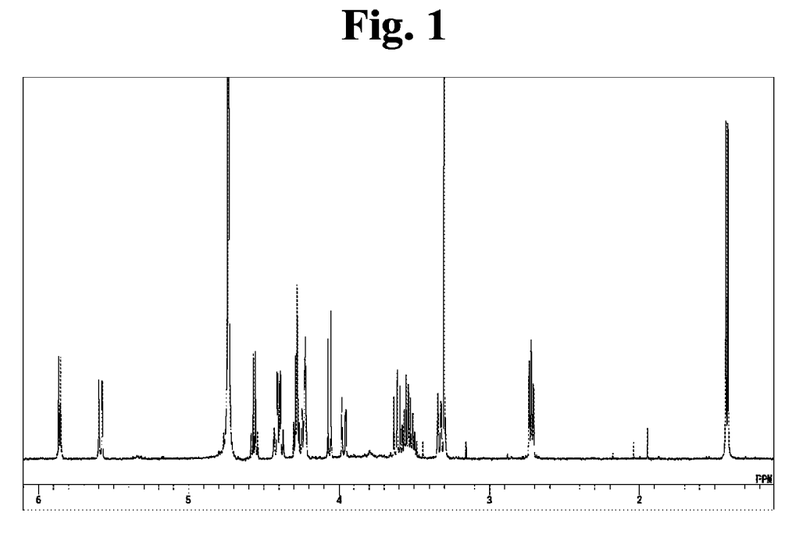
FIG. 1 shows the $^1$H-nuclear magnetic resonance spectrum of compound A-87774-1.
Figure 2:
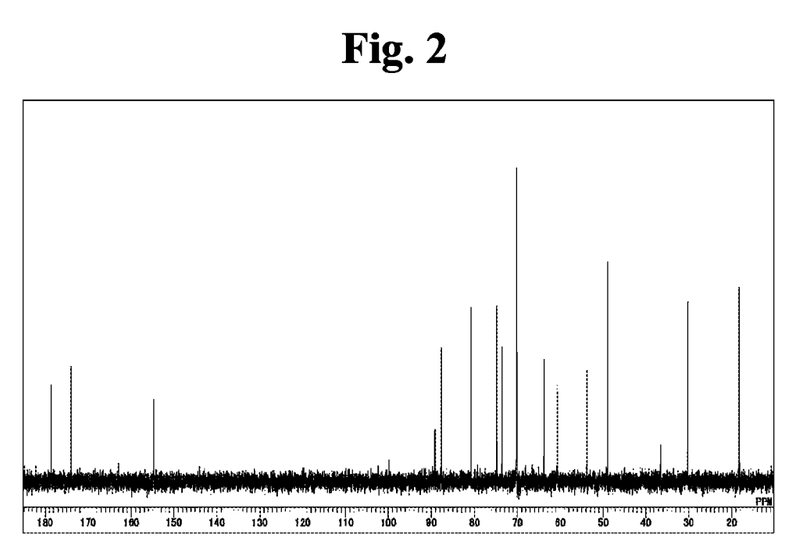
FIG. 2 shows the $^{13}$C-nuclear magnetic resonance spectrum of compound A-87774-1.
Figure 3:
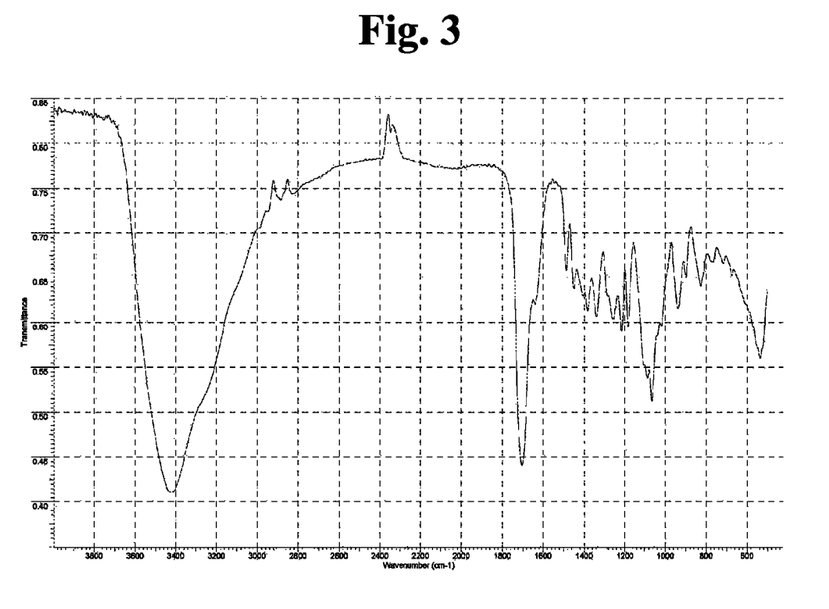
FIG. 3 shows the infrared absorption spectrum of compound A-87774-1.
Figure 4:
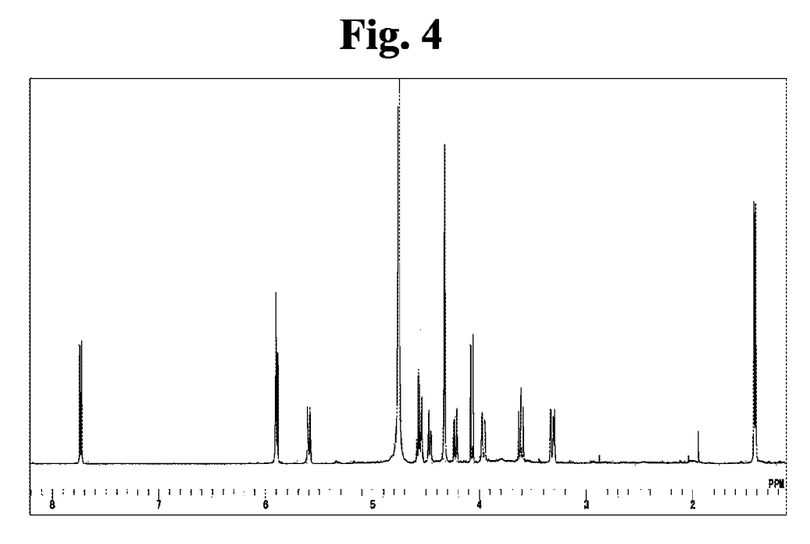
FIG. 4 shows the $^1$H-nuclear magnetic resonance spectrum of compound A-87774-2.
Figure 5:
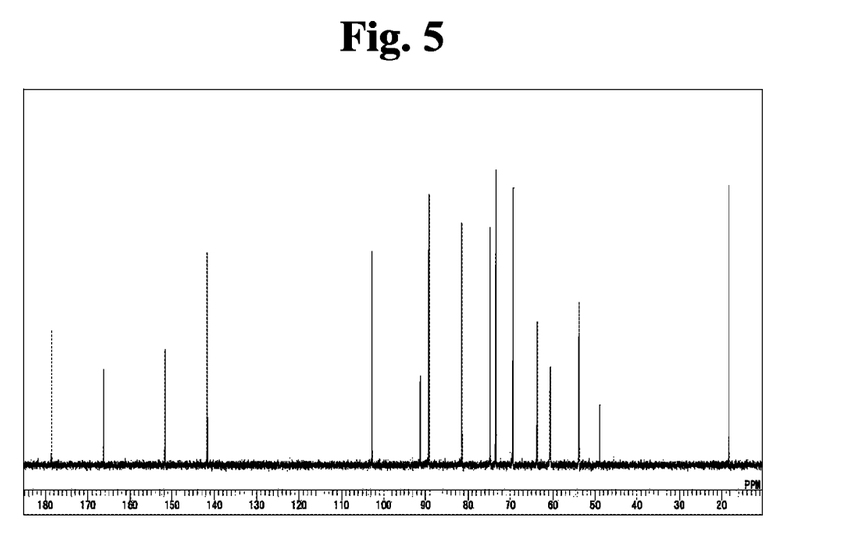
FIG. 5 shows the $^{13}$C-nuclear magnetic resonance spectrum of compound A-87774-2.
Figure 6:
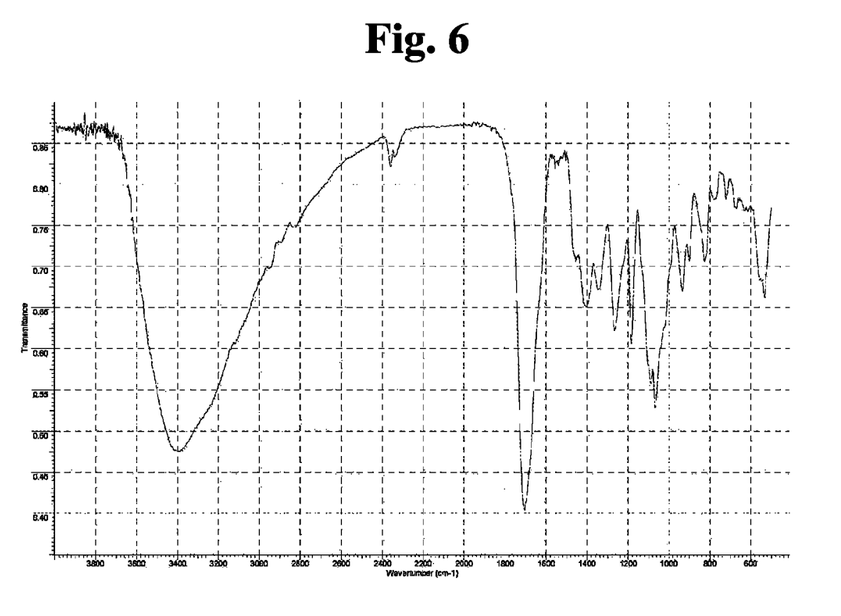
FIG. 6 shows the infrared absorption spectrum of compound A-87774-2.

These compounds A-87774-1 and A-87774-2 had a molecular weight, a molecular formula, a $^1H$-nuclear magnetic resonance spectrum when measured in deuterated water, a $^{13}C$-nuclear magnetic resonance spectrum when measured in deuterated water, an infrared absorption spectrum when measured by KBr disc and a specific optical rotation, which are mentioned above. The $^1$H-nuclear magnetic resonance spectrum, the $^{13}$C-nuclear magnetic resonance spectrum and the infrared absorption spectrum of compound A-87774-1 are shown in FIG. 1, FIG. 2 and FIG. 3 respectively, and the $^1$H-nuclear magnetic resonance spectrum, the $^{13}$C-nuclear magnetic resonance spectrum and the infrared absorption spectrum of compound A-87774-2 are shown in FIG. 4, FIG. 5 and FIG. 6 respectively. It should be noted that methanol was added as the internal standard material for the $^1$H-nuclear magnetic resonance spectrum and the $^{13}$C-nuclear magnetic resonance spectrum of A-87774-1 and A-87774-2.

The measuring equipments are as follows:
Nuclear magnetic resonance spectrum: JEOL ECA500
Infrared absorption spectrum: SHIMADZU FTIR-8400
Specific optical rotation: JASCO DIP-360.

Further, the conditions for measurement of NMR are as follows:

| Frequency | $^1$H: 500.16 MHz, $^{13}$C: 125.77 MHz |
|---|---|

Temperature for measurement, Number of integration steps:

| A-87774-1 | $^1$H: 23.9° C., 8 times, |
| | $^{13}$C: 24.6° C., 21600 times, |
| A-87774-2 | $^1$H: 23.1° C., 8 times, |
| | $^{13}$C: 24.6° C., 46000 times. |

Example 2

Separation of Compound A-87774-3

(1) Culture of Strain SANK 61805

80 mL of a medium having the same composition as the above Example 1 (1) was put into 4 of 500 mL volume Erlenmeyer flasks each, and heated and sterilized at 121° C. for 30 minutes. To each medium, one platinum loop of *Streptomyces* sp. strain SANK 61805 was inoculated from a slant, and cultured at 28° C. and at 210 rpm under rotational shaking Glycerol was added on the 7th day and the 14th day until 2% equivalent, followed by culturing for 22 days.

(2) Separation of Compound A-87774-3

320 mL of the culture solution obtained in the above (1) was separated into a fungal component and a liquid portion by a centrifuge (7500×g). The fungal component portion was stirred together with methanol, and subsequently filtered on diatomaceous earth. After the filtrate was concentrated under reduced pressure, it was combined with the liquid portion of the culture solution and concentrated. This was passed through the activated carbon column (inner diameter 1.6 cm, length 16 cm) to adsorb the active ingredient. The column was washed sequentially with 120 mL water, methanol/water (1/1), and methanol, and subsequently the active ingredient was eluted with 120 mL methanol/2.8% aqueous ammonia (4/1). This was concentrated, subsequently dissolved in 3 mL water, and passed through Dowex 50W×8 column (H$^+$ type: inner diameter 1.2 cm, length 9.5 cm), and the elution and 50 mL water used to wash the column were combined. Then, this was passed through Amberlite CG-400 type I column (Cl$^-$ type: inner diameter 1.8 cm, length 12 cm). Into the column, 60 mL of 0.02N-HCl, 80 mL of 0.02N-HCl containing 0.01M-NaCl, and 200 mL of 0.02N-HCl containing 0.6M-NaCl were sequentially flushed, and fractionated into 20 mL each portion, whereupon the active ingredients were eluted from 5th to 14th portions. In order to remove NaCl, this fraction was passed through the activated carbon column (inner diameter 1.2 cm, length 10 cm) again, and the column was washed with 50 mL water. Subsequently, the active ingredient was eluted with 50 mL methanol/2.8% aqueous ammonia (4/1), and the solvent was distilled off under reduced pressure to give 237 mg of the solid product.

This solid product was purified by high performance liquid chromatography (HPLC). As the HPLC column, Shiseido CAPCELL-PAK C18 UG120 Å (inner diameter 2 cm, length 25 cm) was used, and as the eluent, a mixed solvent of acetonitrile, water and acetic acid (volume mixing ratio: 3/97/0.4) was used, to carry out elution at a column oven temperature of 40° C., and at a flow rate of 10 mL/min, giving 7.3 mg of compound A-87774-3 as a white powder eluted at a retention time between 12.5 and 16.8 minutes.

Figure 7:
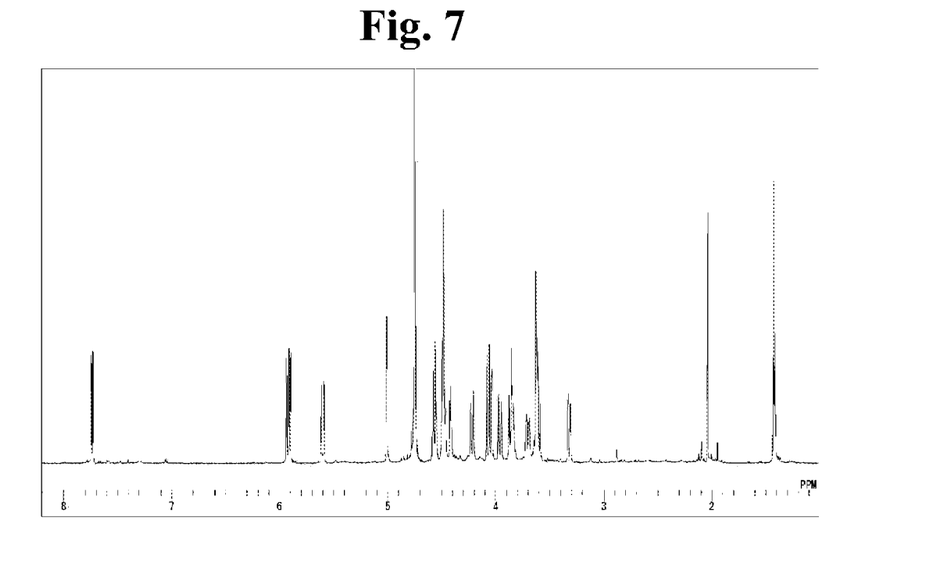
FIG. 7 shows the $^1$H-nuclear magnetic resonance spectrum of compound A-87774-3.
Figure 8:
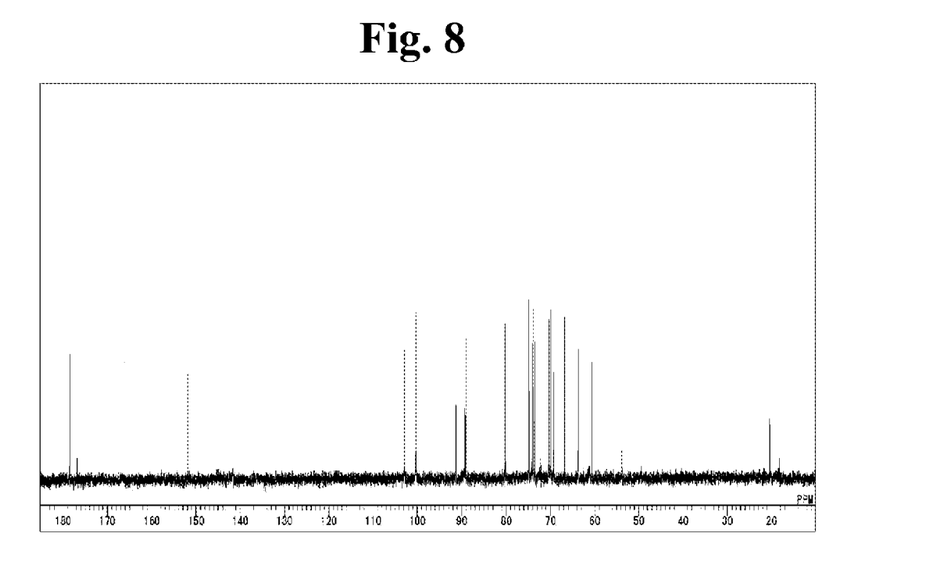
FIG. 8 shows the $^{13}$C-nuclear magnetic resonance spectrum of compound A-87774-3.
Figure 9:
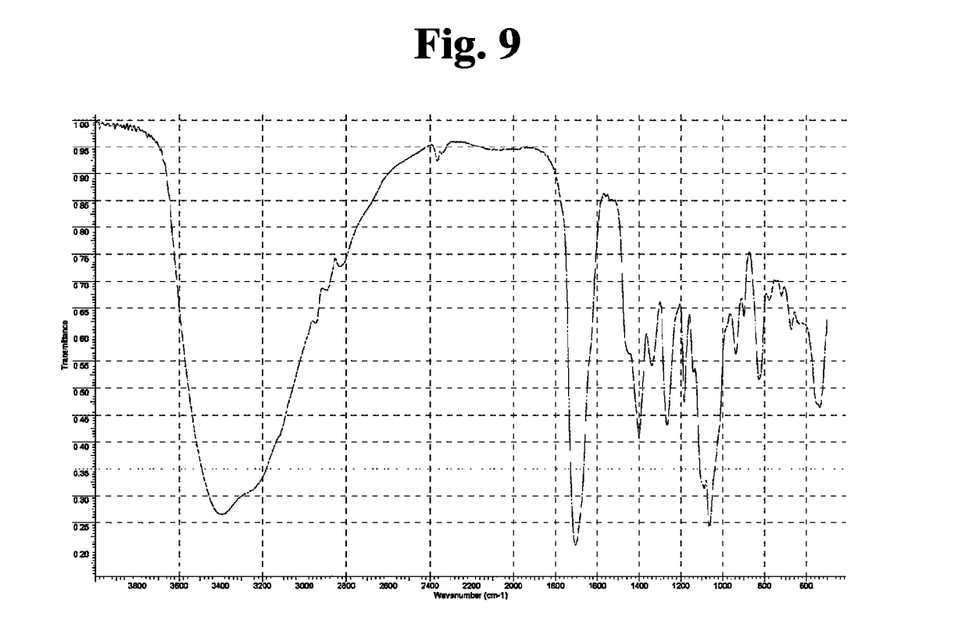
FIG. 9 shows the infrared absorption spectrum of compound A-87774-3.

This compound A-87774-3 had a molecular weight, a molecular formula, a $^1$H-nuclear magnetic resonance spectrum when measured in deuterated water, a $^{13}$C-nuclear magnetic resonance spectrum when measured in deuterated water, an infrared absorption spectrum when measured by KBr disc and a specific optical rotation, which are mentioned above. The $^1$H-nuclear magnetic resonance spectrum, the $^{13}$C-nuclear magnetic resonance spectrum and the infrared absorption spectrum of compound A-87774-3 are shown in FIG. 7, FIG. 8 and FIG. 9 respectively. It should be noted that acetone was added as the internal standard material for the $^1$H-nuclear magnetic resonance spectrum of A-87774-3, and acetic acid was added for the $^{13}$C-nuclear magnetic resonance spectrum of A-87774-3.

The measuring equipments are as follows:
Nuclear magnetic resonance spectrum: JEOL ECA500
Infrared absorption spectrum: SHIMADZU FTIR-8400
Specific optical rotation: JASCO DIP-360.

Further, the conditions for measurement of NMR are as follows:

| Frequency | $^1$H: 500.16 MHz, $^{13}$C: 125.77 MHz |
|---|---|

Temperature for measurement, Number of integration steps:

| A-87774-3 | $^1$H: 23.1° C., 64 times, |
| | $^{13}$C: 23.9° C., 48000 times. |

Test Example 1

Spray Test for Stems and Leaves

Compounds A-87774-1, A-87774-2 and A-87774-3 were dissolved in an aqueous solution containing 0.1% (W/V) Newcol 1200 to prepare 100 and 50 mg/L solutions. Granular paddy field soil was put into a 4 cm cube pot, in which seeds of wild mustard, velvetleaf, redroot pigweed and barnyard grass were inoculated, and cultivated in a green house for 7 days to obtain a plant body, which was sprayed with 0.5 mL of this test solution, and the herbicidal efficacy was investigated 14 days after. The herbicidal efficacy was evaluated to 6 grades of 5 (death) to 0 (no activity). These results are shown in Table 4.

TABLE 4

| Compound | A-87774-1 | | | | A-87774-2 | | | | A-87774-3 | | | |
| --- | --- | --- | --- | --- | --- | --- | --- | --- | --- | --- | --- | --- |
| concentration (mg/L) | wild mustard | velvetleaf | redroot pigweed | barnyard grass | wild mustard | velvetleaf | redroot pigweed | barnyard grass | wild mustard | velvetleaf | redroot pigweed | barnyard grass |
| 100 | 5 | 5 | 5 | 1 | 5 | 5 | 5 | 5 | 5 | 5 | 5 | 3 |
| 50 | 5 | 5 | 5 | 1 | 5 | 5 | 5 | 3 | 5 | 5 | 5 | 1 |

From these results, it was found that all of A-87774 compounds show excellent herbicidal effects.

Test Example 2

Spray Test for Stems and Leaves

In a plastic pot [10 cm×15 cm×3 cm (height)] in which paddy field soil was placed, a test plant shown in Table 2 was inoculated, and 14 days after the inoculation, A-87774-2 was sprayed on the plant. A 100 mg/L solution dissolved in an aqueous solution containing 0.01% (v/v) gramin S was prepared as the drug solution, and sprayed in a liquid amount of equivalent to 2000 L/ha (dosage 200 g/ha). The herbicidal efficacy was investigated 14 days after, and evaluated to 6 grades of 5 (death) to 0 (no activity). These results are shown in Table 5.

TABLE 5

| Dosage of | A-87774-2 | | | | | | | | | |
| --- | --- | --- | --- | --- | --- | --- | --- | --- | --- | --- |
| compound (g/ha) | barnyard grass | southern crabgrass | ryegrass | wild oat | yellow nutsedge | velvetleaf | prickly sida | redroot pigweed | wild mustard | black nightshade |
| 200 | 2 | 5 | 5 | 4 | 5 | 5 | 5 | 5 | 5 | 5 |

From these results, it was found that compound A-87774-2 shows excellent herbicidal effects over a wide range of weeds.

Test Example 3

Spray Test for Stems and Leaves

In a plastic pot [10 cm×15 cm×3 cm (height)] in which paddy field soil was placed, 9 types of specimen plants were inoculated, and 14 days after the inoculation, a solution of 62.5 mg/L of A-87774-2, or 250 mg or 62.5 mg/L of A-87774-3 dissolved in an aqueous solution containing 0.1% (w/v) Newcol 1200 in a liquid amount of equivalent to 2000 L/ha were sprayed on the plants. The dosage was 125 g/ha, 500 g/ha, and 125 g/ha respectively. The herbicidal efficacy was investigated 15 days after, and evaluated to 6 grades of 5 (death) to 0 (no activity). These results are shown in Table 6.

TABLE 6

| Dosage of compound (g/ha) | barnyard grass | southern crabgrass | ryegrass | stiff darnel | green foxtail | velvetleaf | tall morning glory | redroot pigweed | wild mustard |
| --- | --- | --- | --- | --- | --- | --- | --- | --- | --- |
| A-87774-2 | | | | | | | | | |
| 125 | 5 | 5 | 4 | 5 | 5 | 5 | 5 | 5 | 5 |
| A-87774-3 | | | | | | | | | |
| 500 | 5 | 5 | 5 | 5 | 5 | 5 | 5 | 5 | 5 |
| 125 | 2 | 5 | 0 | 1 | 5 | 5 | 5 | 5 | 5 |

From these results, it was found that compound A-87774-3 also shows excellent herbicidal effects over a wide range of weeds.

Test Example 4

Soil Treatment Test

In a plastic pot [10 cm×15 cm×3 cm (height)] in which paddy field soil was placed, 7 types of specimen plants were inoculated, and 1 day after, a drug solution of 50 mg/L or 12.5 mg/L of A-87774-2 or A-87774-3 was dropped for treatment, and the degree of growth suppression was investigated 14 days after. The dosage of the drug solution was 500 g/ha, and 125 g/ha respectively. The herbicidal efficacy was evaluated to 6 grades of 5 (not germinated) to 0 (no activity). These results are shown in Table 7.

TABLE 7

| Dosage of compound (g/ha) | A-87774-2 | | | | | | | A-87774-3 | | | | | | |
|---|---|---|---|---|---|---|---|---|---|---|---|---|---|---|
| | barnyard grass | southern crabgrass | rye-grass | velvet-leaf | tall morning glory | redroot pigweed | wild mustard | barnyard grass | southern crabgrass | rye-grass | velvet-leaf | tall morning glory | redroot pigweed | wild mustard |
| 500 | 5 | 5 | 5 | 5 | 5 | 5 | 5 | 5 | 5 | 5 | 5 | 5 | 5 | 5 |
| 125 | 1 | 5 | 5 | 0 | 5 | 5 | 5 | 4 | 5 | 5 | 0 | 5 | 5 | 5 |

From these results, it was found that compounds A-87774 show excellent herbicidal effects also in soil treatment.

Test Example 5

Paddy Field Treatment Test

A container with a diameter of 6 cm in which paddy field soil was placed and filled with water, followed by soil puddling, and subsequently seeds or tubers of 6 types of paddy field weeds were planted. 2 days after, a drug solution of 50 mg/L of A-87774-2 or A-87774-3 was dropped for treatment, and the degree of growth suppression was investigated 26 days after. The dosage of the drug solution was allowed to be 500 g/ha. The herbicidal efficacy was evaluated to 6 grades of 5 (not germinated) to 0 (no activity). These results are shown in Table 8.

TABLE 8

| Dosage of compound (g/ha) | A-87774-2 | | | | | | A-87774-3 | | | | | |
|---|---|---|---|---|---|---|---|---|---|---|---|---|
| | early water-grass | Japanese bulrush | dwarf arrow-head | arrow-head | tidalmarsh flatsedge | Kuroguwai | early water-grass | Japanese bulrush | dwarf arrow-head | arrow-head | tidalmarsh flatsedge | Kuroguwai |
| 500 | 5 | 5 | 5 | 5 | 5 | 5 | 5 | 5 | 5 | 5 | 5 | 5 |

From these results, it was found that compounds A-87774 show excellent herbicidal effects also over paddy field weeds.

INDUSTRIAL APPLICABILITY

The novel compounds A-87774-1, A-87774-2 and A-87774-3 of the present invention have an excellent herbicidal activity and plant growth regulating activity, and are useful as an agrochemical (in particular, a herbicide for agriculture and horticulture and a plant growth regulator).

DEPOSITORY NUMBER

FERM BP-10840

The invention claimed is:
1. A compound A-87774 selected from the group consisting of:
(I) a compound A-87774-1 having the following properties:
1) Molecular weight: 668,
2) Molecular formula: $C_{18}H_{29}N_4O_{17}PS_2$,
3) $^1$H-nuclear magnetic resonance spectrum ($\delta_{ppm}$) when measured in deuterated water: 5.86 (1H, d, J=5.9 Hz), 5.59 (1H, d, J=11.0 Hz), 4.56 (1H, q, J=6.9 Hz), 4.42 (1H, dd, J=11.2, 2.9 Hz), 4.38 (1H, dd, J=11.2, 3.7 Hz), 4.30-4.27 (2H, m), 4.24-4.23 (2H, m), 4.07 (1H, d, J=10.1 Hz), 3.97 (1H, dd, J=12.7, 2.1 Hz), 3.61 (1H, dd, J=11.3, 10.3 Hz), 3.55 (1H, m), 3.52 (1H, m), 3.33 (1H, dd, J=11.4, 1.8 Hz), 2.72 (1H, dd, J=7.0, 6.6 Hz), 1.42 (3H, d, J=6.9 Hz),
4) $^{13}$C-nuclear magnetic resonance spectrum ($\delta_{ppm}$) when measured in deuterated water: 178.6 (s), 174.0 (s), 154.8 (s), 91.4 (s), 89.2 (d), 87.6 (d), 80.8 (d), 74.8 (d), 73.5 (d), 70.2 (d), 70.2 (d), 70.0 (t), 63.7 (d), 60.6 (d), 53.8 (t), 36.5 (t), 30.3 (t), 18.3 (q),
5) Infrared absorption spectrum ($v_{max}$cm$^{-1}$) when measured by KBr disc: 3423, 1703, 1639, 1487, 1450, 1406, 1383, 1339, 1258, 1217, 1184, 1088, 1067, 937, 899, 827, 536, and
6) Specific optical rotation: $[\alpha]_D^{24}$+40.0° (c, 0.22, in $H_2O$), or a salt thereof;
(II) a compound A-87774-2 having the following properties:
1) Molecular weight: 666,
2) Molecular formula: $C_{18}H_{27}N_4O_{17}PS_2$,
3) $^1$H-nuclear magnetic resonance spectrum ($\delta_{ppm}$) when measured in deuterated water: 7.73 (1H, d, J=8.1 Hz), 5.91 (1H, d, J=2.4 Hz), 5.90 (1H, d, J=8.1 Hz), 5.60 (1H, d, J=10.8 Hz), 4.57 (1H, q, J=6.9 Hz), 4.55 (1H, d, J=11.4 Hz), 4.46 (1H, dd, J=11.2, 2.2 Hz), 4.34-4.32 (3H, m), 4.22 (1H, d, J=12.6 Hz), 4.07 (1H, d, J=10.1 Hz), 3.96 (1H, dd, J=12.6, 1.7 Hz), 3.61 (1H, dd, J=11.4, 10.1 Hz), 3.32 (1H, d, J=11.4 Hz), 1.42 (3H, d, J=6.9 Hz),
4) $^{13}$C-nuclear magnetic resonance spectrum ($\delta_{ppm}$) when measured in deuterated water: 178.6 (s), 166.3 (s), 151.8

(s), 141.7 (d), 102.8 (d), 91.3 (s), 89.3 (d), 89.2 (d), 81.5 (d), 74.8 (d), 73.5 (d), 73.4 (d), 69.5 (d), 69.4 (t), 63.7 (d), 60.6 (d), 53.8 (t), 18.3 (q),

5) Infrared absorption spectrum ($\nu_{max} cm^{-1}$) when measured by KBr disc: 3399, 1706, 1455, 1405, 1346, 1266, 1185, 1087, 1067, 934, 900, 826, 534, and 6) Specific optical rotation: $[\alpha]_D^{24} +47.2°$ (c, 1.0, in $H_2O$), or a salt thereof; and (III) a compound A-87774-3 having the following properties:

1) Molecular weight: 828,

2) Molecular formula: $C_{24}H_{37}N_4O_{22}PS_2$,

3) $^1$H-nuclear magnetic resonance spectrum ($\delta_{ppm}$) when measured in deuterated water: 7.74 (1H, d, J=8.1 Hz), 5.94 (1H, d, J=5.3 Hz), 5.91 (1H, d, J=8.1 Hz), 5.60 (1H, d, J=11.0 Hz), 5.01 (1H, br.s), 4.57 (1H, q, J=6.9 Hz), 4.57 (1H, m), 4.50-4.48 (3H, m), 4.41 (1H, m), 4.22 (1H, d, J=12.5 Hz), 4.07 (1H, d, J=10.1 Hz), 4.04 (1H, dd, J=3.3, 1.8 Hz), 3.96 (1H, dd, J=12.5, 1.3 Hz), 3.87 (1H, d, J=12.3 Hz), 3.85 (1H, m), 3.71 (1H, dd, J=12.3, 4.4 Hz), 3.63-3.61 (3H, m), 3.32 (1H, d, J=11.4 Hz), 1.42 (3H, d, J=6.9 Hz), 4) $^{13}$C-nuclear magnetic resonance spectrum ($\delta_{ppm}$) when measured in deuterated water: 178.6 (s), 166.3 (s), 151.8 (s), 141.6 (d), 102.9 (d), 100.3 (d), 91.3 (s), 89.2 (d), 89.1 (d), 80.2 (d), 74.8 (d), 74.1 (d), 73.8 (d), 73.5 (d), 72.2 (d), 70.3 (d), 69.9 (d), 69.3 (t), 66.8 (d), 63.7 (d), 61.0 (t), 60.6 (d), 53.7 (t), 18.3 (q), 5) Infrared absorption spectrum ($\nu_{max} cm^{-1}$) when measured by KBr disc: 3396, 1705, 1402, 1340, 1265, 1184, 1090, 1063, 937, 899, 825, 538, and 6) Specific optical rotation: $[\alpha]_D^{24} +78.7°$ (c, 1.0, in $H_2O$), or a salt thereof.

2. A method for producing the compound according to claim 1, comprising culturing a microorganism belonging to *Streptomyces* genus, and obtaining the compound from the culture.

3. An agrochemical containing the compound according to claim 1 as an active ingredient.

4. A herbicide containing the compound according to claim 1 as an active ingredient.

5. A plant growth regulator containing the compound according to claim 1 as an active ingredient.

6. A method for treating weeds, comprising treating weeds or soil with the compound according to claim 1.

7. The method according to claim 6, wherein the weeds are weeds in an upland field and/or weeds in a paddy field.

8. A method for regulating plant growth, comprising treating a plant body with the compound according to claim 1.

* * * * *